United States Patent [19]
Sobczak et al.

[11] Patent Number: 6,051,426
[45] Date of Patent: Apr. 18, 2000

[54] VECTORS FOR TRANSFORMING CHO CELLS

[75] Inventors: Elaine Sobczak, Paris; Yves Malpiece, deceased, late of Amiens, by Isabelle Vidal, legal representative; Marie-Louise Michel, Paris; Pierre Tiollais, Paris; Rolf E. Streeck, Paris, all of France

[73] Assignee: Institut Pasteur, Institut National de la Sante et de la Recherche Medicale and Centre National de la Recherche Scientifique, Paris, France

[21] Appl. No.: 08/384,249

[22] Filed: Feb. 6, 1995

Related U.S. Application Data

[62] Continuation of application No. 08/195,201, Feb. 14, 1994, abandoned, which is a division of application No. 07/662,993, Feb. 28, 1991, Pat. No. 5,324,513, which is a continuation of application No. 07/431,718, Nov. 3, 1989, abandoned, which is a continuation of application No. 07/163,185, Feb. 25, 1988, abandoned, which is a continuation of application No. 06/800,650, filed as application No. PCT/FR85/00044, Mar. 7, 1985, abandoned.

[30] Foreign Application Priority Data

Mar. 7, 1984 [FR] France .................................. 84 03564

[51] Int. Cl.$^7$ .............................. C12N 5/10; C12N 15/85
[52] U.S. Cl. ........................................ 435/362; 435/320.1
[58] Field of Search ................................ 435/69.1, 172.1, 435/172.3, 240.2, 320.1, 362, 325, 352

[56] References Cited

U.S. PATENT DOCUMENTS

| | | | |
|---|---|---|---|
| 4,113,712 | 9/1978 | Funakoshi | 530/380 |
| 4,118,478 | 10/1978 | Prince | 424/227.1 |
| 4,428,941 | 1/1984 | Galibert et al. | 514/2 |
| 4,554,157 | 11/1985 | Skelly et al. | 424/227.1 |
| 4,722,840 | 2/1988 | Valenzuela et al. | 424/192.1 |
| 5,024,938 | 6/1991 | Nozaki et al. | 435/68.1 |
| 5,098,704 | 3/1992 | Valenzuela | 424/277.1 |
| 5,670,530 | 9/1997 | Thill | 530/403 |

FOREIGN PATENT DOCUMENTS

| | | |
|---|---|---|
| 0 020 251 | 12/1980 | European Pat. Off. . |
| 038 765 | 10/1981 | European Pat. Off. . |
| 0 009 930 | 7/1982 | European Pat. Off. . |
| 0 174 444B1 | 3/1992 | European Pat. Off. . |

OTHER PUBLICATIONS

Christman et al., "Amplification of Expression of Hepatitis B Surface Antigen in 3T3 Cells Cotransfected with a Dominant–Acting Gene and Cloned Viral DNA", PNAS, vol. 79, pp. 1815–1819, Mar. 1982.

Kaufman et al., "Amplification and Expression of Sequences Cotransfected with a Modular Dihydrofolate Reductase Complementary DNA Gene," J. Mol. Biol., vol. 159, pp. 601–621, 1982.

Subramani et al., "Analysis of Gene Expression Using Simian Virus 40 Vectors", Anal. Biochem., vol. 135, pp. 1–15, 1983.

Chakrabaotz et al. "Identification of Integrated Hepatitis B Virus DNA and Expression of Viral RNA in an HBsAg–Producing Human Hepatocellular Carcinoma Cell Line", Nature, vol. 286 Jul. 31, 1980, pp. 531–533.

Malpiece et al. "The Gene S Promoter of Hepatitis B Virus Confers Constitutive Gene Expression", Nucleic Acids Res., vol. 11, No. 13, 1983, pp. 4645–4654.

Pourcel et al. "Transcription of the Hepatitis B Surface Antigen Gene in Mouse Cells Transformed with Cloned Viral DNA", J. of Virol., Apr. 1982, vol. 42, No. 1, pp. 100–105.

Edman et al. "Integration of Hepatitis B Virus Sequences and Their Expression in a Human Hepatoma Cell", Nature, vol. 286, Jul. 31, 1980, pp. 535–538.

Alberti et al., "Virus Receptors for Polymerized Human Serum Albumin and Antireceptor Antibody in Hepatitis B Virus Infection," Prog. Clin. Biol. Res., 143: 327–336 (1983).

Mitsunobu et al., "A Receptor for Polymerized Human and Chimpanzee Albumins on Hepatitis B Virus Particles Co–occurring with HBeAg," Gastroeneterology, 76(2): 242–247 (1979).

Jacobs et al., "Simultaneous Synthesis and Assembly of Various Hepatitis B Surface Proteins in *Saccharomyuces cerevisiae*," Gene, 80: 279–291 (1989).

Lenkei et al., "Receptors for Polymerized Albumin on Liver Cells," Experientia, 33/8: 1046–1047 (1977).

Machida et al., "A Hepatitis B Surface Antigen Polypeptide (P31) With the Receptor for Polymerized Human as Well as Chimpanzee Albumins," Gastroenterology, 85(2): 268–274 (1983).

Michel et al., "Synthesis in Animal Cells of Hepatitis B Surface Antigen Particles Carrying a Receptor for Polymerized Human Serum Albumin," Proc. Natl. Acad. Sci. (USA), 81: 7708–7712 (1984).

Milich et al., "Characterization of the Interaction Between Polymerized Human Albumin and Hepatitis B Surface Antigen," Gastroenterology, 81(2): 218–225 (1981).

(List continued on next page.)

*Primary Examiner*—David Guzo
*Attorney, Agent, or Firm*—Finnegan, Henderson Farabow, Garrett & Dunner, L.L.P.

[57] ABSTRACT

The invention concerns a composition useful for the manufacture of vaccines containing particles having the immunogenic properties characteristic of the antigen HBsAg, these particles being more particularly characterized by the fact that the particles equally contain a receptor for polymerized human albumin. They are obtained by transformation of human or animal cells by a vector containing a DNA sequence coding for the S and pre-S regions of a genome of viral hepatitis B, this DNA sequence being placed under the direct control of a promoter permitting the effective transcription of the sequence in the human or animal cells transformable by the vector.

2 Claims, 6 Drawing Sheets

OTHER PUBLICATIONS

Ringold et al., "Co–Expression and Amplification of Dihydrofolate Reductase cDNA and the *Escherichia coli* XGPRT Gene in Chinese Hamster Ovary Cells," J. Mol. Appl. Genet., 1: 165–175 (1981).

Stibbe et al., "Variable Protein Composition of Hepatitis B Surface Antigen from Different Donors," Virology, 123: 436–442 (1982).

Stratowa et al., "Recombinant Retroviral DNA Yielding High Expression of Hepatitis B Surface Antigen," EMBO J., 1(12): 1573–1578 (1982).

Wang et al., "Enhanced Production of Hepatitis B Surface Antigen in NIH 3T3 Mouse Fibroblasts by Using Extrachromosomally Replicating Bovine Papillomavirus Vector," Mol. Cell. Biol., 3(6): 1032–1039 (1983).

Mitsunobu et al., "A Receptor for Polymerized Human and Chimpanzee Albumins on Hepatitis B Virus Particles Co–occurring with HBeAg," Biol. Abstr., 68: 3690 (1979).

Machida et al., "A Hepatitis B Surface Antigen Polypeptide (P31) With the Receptor for Polymerized Human as Well as Chimpanzee Albumins," Biol. Abstr., 77: 12366 (1984).

Milich et al., "Characterization of the Interaction Between Polymerized Human Albumin and Hepatitis B Surface Antigen," Chem. Abstr., 95: 113155 (1981).

Alberti et al., "Virus Receptors for Polymerized Human Serum Albumin and Antireceptor Antibody in Hepatitis B Virus Infection," Chem. Abstr., 100: 172783 (1984).

Burnette, et al., "Properties and Relative Immunogenicity of Various Preparations of Recombinant DNA–derived Hepatitis B Surface Antigen," Chem. Abstr., 103: 121281w.

VECTORS FOR TRANSFORMING CHO CELLS

This application is a continuation of application Ser. No. 08/195,201, filed Feb. 14, 1994, now abandoned, which is a division of application Ser. No. 07/662,993, filed Feb. 28, 1991, issued as U.S. Pat. No. 5,324,513, which is a continuation of application Ser. No. 07/431,718, filed Nov. 3, 1989, now abandoned, which is a continuation of application Ser. No. 07/163,185, filed Feb. 25, 1988, now abandoned, which is a continuation of application Ser. No. 06/800,650, filed Jan. 7, 1987, now abandoned, filed as PCT application PCT/FR85/00044 filed on Mar. 7, 1985.

The invention concerns a composition useful for the fabrication of vaccines, containing or formed by approximately spherical polypeptide particles, at least as concerns most of them, these particles having immunogenic and immunologic properties characteristic of the surface antigen of the virus of viral hepatitis B. This antigen is often designated by the abbreviation HBsAg or yet more simply HBs. It equally concerns the eucaryotic cell lines, preferably animal, capable of excreting into their culture medium polypeptide particles of the kind indicated above with elevated production yields and the means, notably modified vectors, permitting such cell lines to be obtained.

One will recall first that the serum of chronic carriers of the virus of hepatitis B (HBV) contains empty viral envelopes in the form of particles or filaments of 22 nm diameter and sometimes the complete infectious virions, spherical particles of 42 nm. The viral envelope bears the surface antigen (HBsAg) and the presence of infectious virions is generally accompanied by a soluble antigen called antigen (HBeAg).

The polypeptide composition of the viral envelope has been much studied (Robinson W. S. (1977) Ann. Rev. Microbiol. 31, 357–377). It includes a major polypeptide present in glyosylated form (GP29) and non-glycosylated (P25) and at least three minor polypeptides called GP33, GP36 and P41. The polypeptides GP33 and GP36 may have the same sequence in amino acids. GP36 would possess only one supplementary sugar residue (Stibbe W. and Gerlich W. H. (1983) J. Virology 46, 626–628). The relative quantity of minor proteins in relation to the major polypeptide varies from one plasma to another. It is very superior in HBeAg positive serums rich in viral particles. The polypeptides GP33 and GP36 may then represent several % of the proteins of the envelope while they represent less than 1% in non-infectious HBeAg negative serums (Stibbe W. and Gerlich W. H. (1982) Virology 123, 436–442).

The major polypeptide of the envelope is constituted of 226 amino acids and is coded by the gene S. The polypeptide sequence of GP33 and GP36 may be coded by the S gene and a part of the pre-S region. In this hypothesis, this polypeptide sequence would have the same C-terminal end as the major polypeptide and would contain a supplementary sequence of 55 amino acids in the N-terminal position (Stibbe W. and Gerlich W. H. (1983), J. Virology 46, 626–628).

Recently, it has been shown that the viral particles isolated from an HbeAg positive serum contain a receptor for polymerized human albumin (pHSA) (Machida A. et al (1983) Gastroenterology 85, 268–274). This receptor may be carried by polypeptides GP33 and GP36. Thanks to this receptor, the pHSA may form a bridge between the viral particle and the hepatocyte, thus permitting the attachment of the virus and it's penetration into the hepatic cell. The appearance of the anti-receptor antibodies may be essential in the process of "clearance" of the virus. In fact, the sero-conversion HBeAg/anti-HBe, initial step of recovery, is accompanied by the appearance of these antibodies, while these are absent during the evolution towards chronicity (Pontisso P. et al (1983) J. of Virolgical Methods 6, 151–159).

In parallel, one observes the disappearance of the antigens corresponding to the pHSA receptor, which appears to bear evidence that the expression of the corresponding gene does not normally occur except in specific situations (notably during the step of the replication of the virus). It is this which is corroborated again by the analysis of the empty natural envelopes of the hepatitis B virus, such as those contained in vaccine preparations currently commercialized and obtained from blood serum from donors who, in the past, have been exposed to the hepatitis B virus. In fact, the analysis by gel electrophoresis on polyacrylamide in the presence of sodium dodecylsulfate (SDS) of polypeptides obtained after dissociation of the natural particles at 100 degrees C. for 5 minutes, in the presence of dithiothreitol (DTT), does not reveal the presence of polypeptides having elevated molecular weights, notably of the order of 34,000. In the same way, the presence of such high molecular weight polypeptides has not been observed in the compositions of particles possessing the immunologic and immunogenic properties of the HBs antigen, such as obtained by the transformation of animal cells transformed by genetic engineering techniques by means of vectors which have been described for example in the European patent application No. 38 765.

The invention has for a goal to furnish vaccine compositions having reinforced protection properties with regard to the hepatitis B virus. It also has for a goal to furnish cell lines transformed by the techniques of genetic engineering, which may be maintained in culture arid which are apt to excrete the active principles of these reinforced vaccine compositions into their culture medium, and this with yields of production much higher than those permitted by most of the genetically transformed cultures currently available. And lastly, it has for a goal to furnish the means (vectors and process) permitting the obtaining of such cell lines from eucaryotic cell lines, notably from mammals, of the sort which are capable of being maintained in culture.

The invention results from the observation that it was possible to induce the expression of genetic sequences which, in the genome of the virus of hepatitis B code for the pHSA receptor, under conditions however very far from those which are prevalent under the specific biological situations which were evoked above. Last, it has been noted that the association in the same vaccine composition of the antigen HBs with the polypeptide fragments carrying an antigenic determinant appearing to correspond to this receptor, led to the reinforced vaccine compositions in question above.

The composition useful for the manufacture of vaccines according to the invention which contains approximately spherical polypeptide particles (or is formed by these particles), at least as concerns most of them (if not all), which have immunogenic and immunologic properties characteristic of the antigen HBsAg, which have sizes of 18 to 25 nm, notably from 20 to 22 nm, and densities permitting their isolation in a density zone of 1.20–1.22 g/ml in CsCl based density gradient, and a level of total purity for there to an absence of any Dane's particles arid HBe antigens, including the HBc, and more particularly characterized by the fact that the said spherical particles equally contain a receptor for polymerized human albumin. More particularly, the polypeptide particles of the invention may be seen to contain substantial proportions of polypeptides having molecular weights of the order of 34,000 daltons, these polypeptides preferably constituting a proportion superior to 10%, and preferably superior to 20% of the total quantity of polypeptide constitutive of the aforesaid particles.

Preferably yet, the composition according to the invention is exempt of any component of human origin, such as one finds in human blood serums. It is a matter essentially of compositions of particles having the immunogenic properties of the antigen HBsAg and of the pHSA receptor which are excreted into their culture medium by cell lines maintained in culture and which have been previously transformed by a vector containing the appropriate coding sequences, the transformation having been accomplished under conditions permitting the effective expression of peptide sequences bearing the immunogenic sites as well as the HBs antigen and the pHSA receptor.

The invention equally concerns the vectors appropriate to the transformation of the eucaryotic cell lines, more particularly of human or animal cells in culture to render them apt to produce the above indicated immunogenic particles. These vectors, which contain a DNA sequence coding for the S and pre-S regions of the genome of the virus of viral hepatitis B, are characterized in that the said sequence of DNA is, within this vector, placed under the direct control of an exogenous promoter of known capacity to permit the effective initiation of the transcription of the genes directly under its control in the eucaryotic cells, notably human or animal, for which the said vectors are intended. One may refer for example to the article by Galibert and coll., 1979. Nature, vol. 281, p. 646–650, about the said DNA sequence. It includes notably the S gene itself preceded by the pre-S sequence containing approximately 165 triplets and whose first nucleotides appear in the partial formulation of the said sequences indicated below:

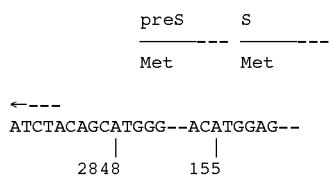

The exogenous promoter used is distinct or foreign vis-à-vis the "endogenous" promoter, normally associated with the S and pre-S genes in the genome of the hepatitis B virus. When these cells originate from the monkey, it is advantageous to have recourse to a promoter issuing from the virus SV40, whose capacity is known to permit the effective initiation of the transcription of adjacent genes in the monkey cells. Advantageously, this promoter corresponds to the "precocious" promoter of the SV40 virus, which normally controls the expression of the small T antigen and equally of the large T antigen.

The invention is not limited however to the utilization of this particular promoter, although it has given particularly favorable results with regard to the production by transformed cells of polypeptides carrying the immunogenic determinants characteristic of the HBs antigen and a pHSA receptor, and to their excretion into the culture medium used. One may equally have recourse for example to the late promoter of SV40 (which controls the expression of the proteins VP1, VP2 and VP3). One may refer to the restriction map of the SV40 virus (J. Tooze, Ed. DNA Tumor Viruses, Cold Spring Harbor, N.Y., 1980, chaps 2–5), to appreciate the relative positions of these promoters and the genes coding for the different antigens which are associated with them.

It goes without saying that one may substitute for the SV40 promoters any other type of promoter known to possess or which may be discovered (to have) the capacity to promote the transcription in the cell lines used of the said sequences coding for the aforesaid S and pre-S regions, as soon as they are placed under their control, with for result the incorporation of these sequences with this promoter in the genome of the receiving cells and/or the capacity conferred to the receiving cells thus transformed to synthesize and to excrete substantial quantities of polypeptides having the immunogenic properties of HBsAg and of the pHSA receptor, the capacity thus acquired then being transmitted to the successive generations issuing from these cells.

The said transformed cells will be called "stable" when the character acquired by the cell lines according to the invention to synthesize the said polypeptides is transmitted from one generation of cells to the others. over at least 10 generations.

As examples of other promoters susceptible to being used, one might mention for example the early promoter of the polyome or the LTR promoters of different retroviruses or again the EA promoter of the adenovirus.

As is well known, the promoters taken from the genomes of the virus from which they originate are preferably accompanied by activating "sequences" which normally precede them (relative to the direction of the transcription of the gene sequences normally placed under their control). As an example of the activating sequences, one may refer to the article in Science, 1983, vol. 219, pages 626 to 631, and Nature 1982, vol. 295, pages 568 to 572.

Advantageously, the aforesaid DNA sequence coding for the aforesaid pre-S and S regions is placed immediately behind a DNA fragment constituted of the promoter and the activating sequence permitting the normal transcription of the pre-S or S sequence. The aforesaid fragment includes notably from 300 to 400 base pairs according to the type of promoter and activating sequences utilized.

Preferably yet, the vector according to the invention also contains a sequence of DNA or a label, such as an enzyme, this label being itself under the control of a distinct promoter weaker than the first promoter mentioned above. This label is preferably constituted of a gene or sequence of DNA coding for dihydrofolate reductase (dhfr). It is to be noted that this label lends itself with a particular advantage to the amplification of the number of copies of this vector in the cells which it is capable of transforming, under the conditions which will be indicated further on.

The second promoter is in most cases equally an exogenous promoter. It may however equally be constituted of one of the natural promoters contained in the genome of viral hepatitis B. A particularly preferred promoter is that which comes from the LTR (a sequence called "Long Terminal Repeat" described in Nature, 1981, 294, 228–232) of the mouse mammary tumor virus (MMTV).

The invention also concerns the cell lines transformed by the vectors such as they have been defined above and which are apt to excrete into their culture medium the immunogenic particles defined above. In particular, it concerns cell lines having a capacity of production of at least 1 microgram, and preferably of at least 10 micrograms of HBsAg per $10^6$ cells and per 24 hours. The invention concerns in particular the lines characterized by the specific HBV-RNAs which are of sizes greater than 2.1 kb, notably of the order of 2.2 to 2.8 kb, preferably 2.6 kb, that one may detect there when the transcription of the S and pre-S regions occurs, normally initiated in the pre-S region. The preferred lines are those in which one may equally detect specific HBV-RNAs having sizes greater than 2.1 kb, notably of the order of 2.2 to 2.8 kb, and preferably yet of the order of 2.4–2.6 kb. In general, one will simultaneously detect specific HBV-RNAs having sizes of the order of 2.1 kb, such as that which results from the transcription of the pre-S and S regions, normally initiated in the pre-S region under the control of an endogenous promoter, under the particular biological conditions referred to above (notably during the course of the replication of the virus of hepatitis B) and specific HBV-RNAs having sizes corresponding to the higher values which have been indicated.

Preferably, the lines according to the invention are formed from mammalian cells, notably from CHO cells.

The invention also concerns a process of production of such cell lines susceptible of being maintained in culture, this process includes the transformation of these lines with a vector such as defined above and the isolation of those of the cultures which simultaneously express the sequences coding for the S and pre-S regions of the genome of the virus of hepatitis B.

Of preference, one has recourse to the complete vector which includes the label under the control of a second promoter, the culture of the transformed lines being then realized in the presence of an inhibitor of the marker, the level of this inhibitor in the culture medium being regulated to a concentration sufficient to provoke an amplification of a number of copies of the gene coding for the label in certain at least of the colonies in culture, amplification which allows both the selection of resistant colonies and the obtaining of the cellular clones which secrete accrued quantities of particles presenting the immunogenic activities characteristic of HBsAg and a pHSA receptor.

Advantageously, the label is constituted of a sequence of DNA (or gene) coding for dhfr and the inhibitor is constituted of methotrexate.

The utilization of a second promoter weaker than the first favors the amplification of the number of copies of the DNA sequence coding for HBsAg and the pHSA receptor. In effect it is in general the clones which contain the greatest number of copies of the sequence coding for the label and, as a consequence, in the preferred cell lines of the invention the greatest number of sequences coding for the pre-S and S regions, which are themselves to survive in the culture medium containing the inhibitor.

The effective clones are advantageously selected in culture media containing from 0.5 to 40 micrograms of methotrexate, notably from 1 to 25 micrograms. It is desirable to realize a pre-amplification in media (which are) poorer in inhibitor, notably from 5 to 150 nM of methotrexate, the clones selected at the end of this first step then being cultured in media containing the higher levels of methotrexate indicated above.

The complementary characteristics of the invention will appear yet in the course of the description which follows of the preferred construction of the vectors used for the transformation of the cell lines of animal origin, from the production of cell lines having a high yield of excretion of particles according to the invention and results susceptible of being obtained. One should equally refer to the drawings in which:

I—CONSTRUCTION OF VECTORS

Figure 1:
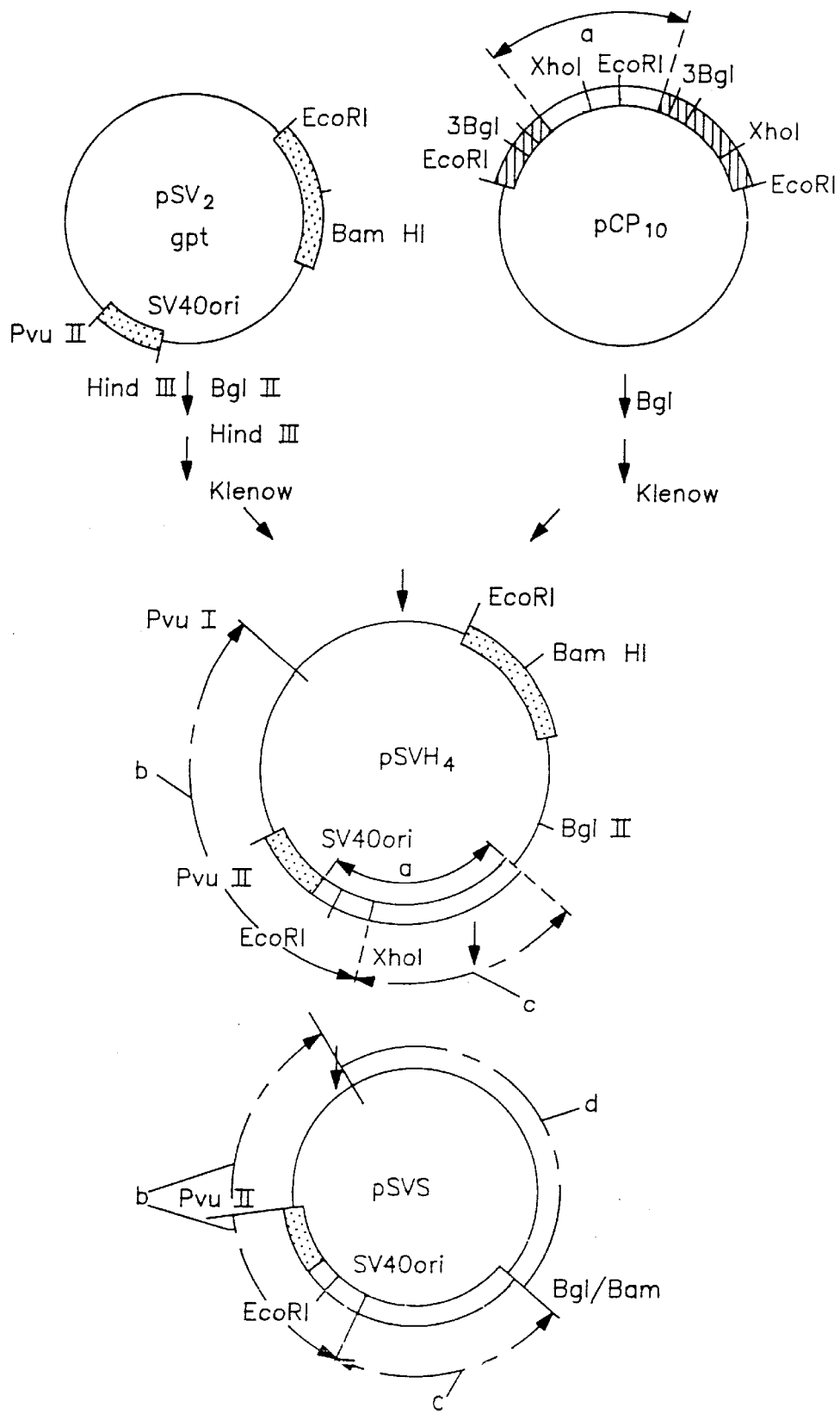
FIGS. 1 and 2 present the essential successive steps of the production of a plasmid conforming to the invention, particularly appropriate to the effective transformation of animal cells, such as the CHO line.

A—Construction of pSVS Plasmid (FIG. 1)

It permits the expression of the S region (the pre-S region and S gene) under the control of the early promoter of the SV40 virus.

The BglII fragment of 2.3 kb has been excised from the pCP10 described in the European patent application No. 81 400634. The pCP10 plasmid is schematized in FIG. 1. The thick and hatched parts are of HBV-DNA origin and the part in thinner lines come from the pBR322 plasmid. The part indicated by the arc a corresponds to the aforesaid fragment of 2.3 kb. pCP10 contains a dimer in tandem head to tail of the HBV genome. This fragment commences ten nucleotides before the ATG of the pre-S region and it terminates 1.1 kb after the TAA stop codon of the S gene. It contains the putative site of the polyadenylation of the mRNA of the HBsAg, and the initiation site of the transcription of the S gene.

One utilizes the early promoter of SV40 contained in the plasmid pSV2 gpt (ATCC 37145) in which the gene of the gpt of E. coli is fused to a PvuII HindIII fragment of 348 bp of the early region of SV40. This fragment includes, other than the origin of the replication of SV40 (SV40 ori), the early and late promoters, the site of the initiation of the transcription of the early messengers and the 72 bp repeated in tandem. pSV2 gpt is schematized in FIG. 1. The thick black parts originate from SV40, the parts on thinner lines from pBR322. The thick while parts contain the pre-S and S regions. The hatched parts correspond to unused sequences of HBV.

The BglII fragment of 2.3 kb, issued from pCP10, has been inserted into the unique HindIII site of the plasmid pSV2 gpt by the ligature of the fragment ends of the DNA rendered open by DNA polymerase (Klenow). After the study of the recombinant plasmids a clone has been selected (pSVH4) in which the region coding for HBS was oriented relative to the SV40 promoter, in a fashion to permit it's expression. The construction has been verified by restriction maps and the nucleotide sequence at the junction of the two fragments SV40 and HBV has been determined.

The plasmid pSVS has been constructed by the ligature of three fragments issued from three plasmids:

1) the fragment of 2.5 kb, PvuI-XhoI issued from pSVH4 (arc b),
2) the fragment of 1.9 kb, XhoI BglII issued from pCP10 (arc c),
3) the fragment of 1.0 kb, BamHI PvuI, from pBR322 (arc d).

The resulting plasmid, pSVS (5.4 kb) differs from pSVH4 by the absence of the gpt region and from the SV40 DNA sequences following after this gpt sequence, and by the presence of the EcoRI-BamHI fragment of pBR322.

Figure 2:
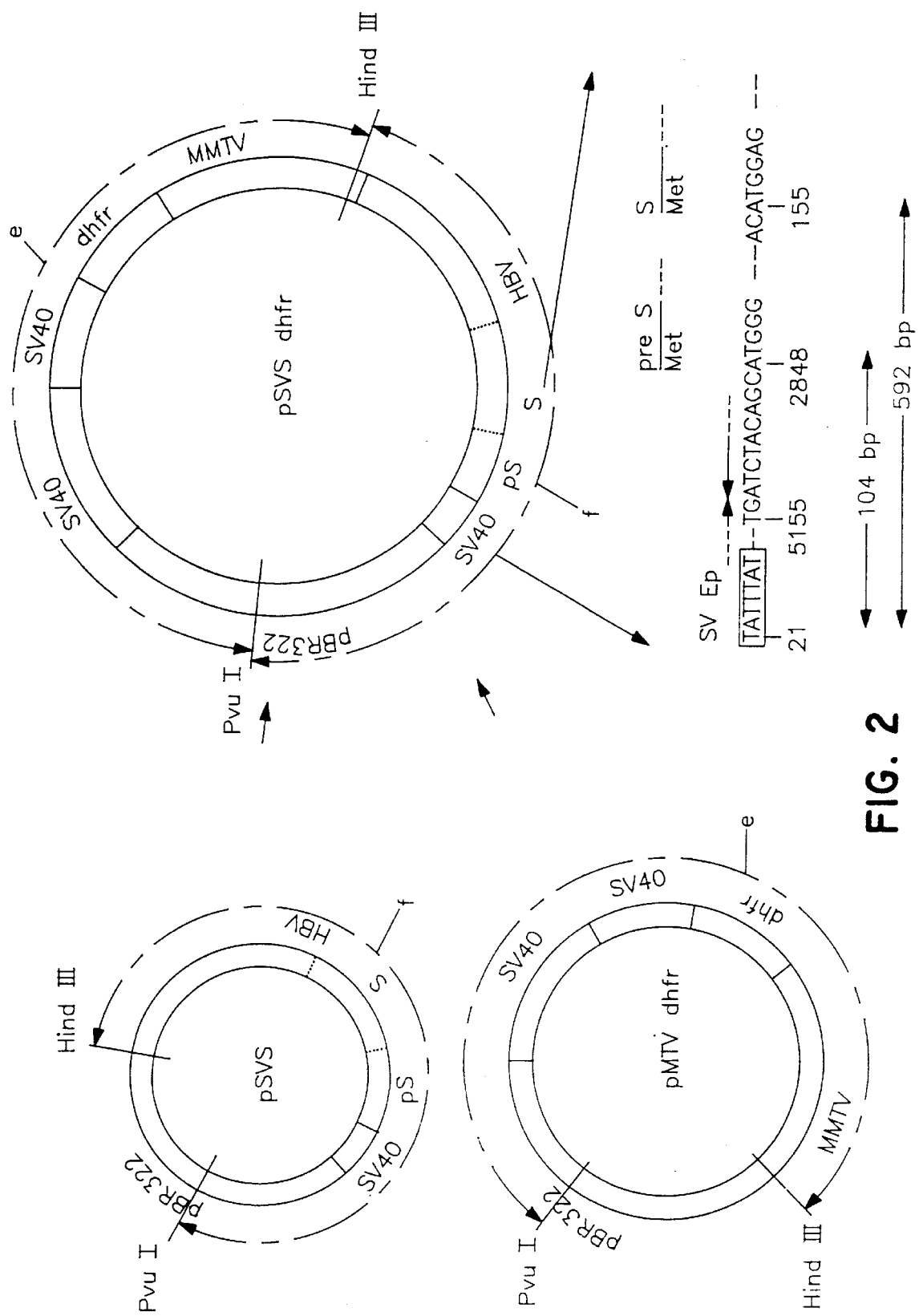

B—Construction of the Plasmid PSVS dhfr (FIG. 2)

One procedes by genetic recombination of the fragments defined under a) and b) hereafter.

a) The fragment containing the dhfr

The plasmid pMTV dhfr described by G. Ringold and coll. (1981) J. of Molecular and Applied Genetics 1: 165–170 (filed with the C.N.C.M. the 7.03.84 under the No. I-286), after linearization by the enzyme PvuI, has then been digested partially by the enzyme HindIII, liberating several fragments of which one of 4400 bp (arc e) containing:

- the LTR of MMTV,
- the cDNA of dhfr,
- the intron of the tAg of SV40,
- the site of polyadenylation of the early genes of SV40,
- an EcoRI-PvuI fragment of pBR322.

b) The HBV DNA fragment

The pSVS plasmid has been digested by PvuI then HindIII, thus liberating a fragment of 4676 bp (arc f) containing:

- the PvuI–PvuII containing the origin of the replication of pBR322;
- the origin of the replication and the early promoter of the SV40 virus;
- the 2.3 kb BglII fragment of HBV containing the parts coding for the pre-S and the S gene, as well as the polyadenylation signal of this gene;
- the BamHI–HindIII fragment of pBR322.

c) Ligature of the fragments

After purification, these two fragments are joined by the homologous sites PvuI and HindIII, thus re-establishing the resistance to ampicillin of pBR322.

In the recombinant vector, the units of transcription of the S region and of the dhfr gene are oriented in the same direction and separated by around 300 bp of pBR322.

The cDNA coding for the dhfr may also be obtained from the pSV2 dhfr (ATCC 337146), pSV3 dhfr (ATCC 37147) or pSV5 dhfr (ETCC 31148).

The placement of the gene of the dhfr under the control of a weak promoter (LTR of MMTV) and of the HBV gene under the control of a strong promoter (early promoter of SV40) increases the efficiency of gene amplification. The nucleotide sequence of the junction between the pre-S region and the early promoter of SV40 has been verified (FIG. 2).

II—TRANSFECTION OF ANIMAL CELLS

1) Transfer and Expression of the Plasmid pSVS dhfr in CHO dhfr⁻:

CHO dhfr⁻ cells (Urlaub G. and Chasin L. A. (1980) P.N.A.S. 77, 4216–4220) (filed with C.N.C.M. the 7.03.84 and under No. I-287) have been transfected according to the technique of Graham and Van der Eb (1973, Virology 52, 456–467) modified by Parker and Stark (1979, J. Virology, 31, 360–369). The production of HBsAg by the CHO dhfr⁺ has been tested by radioimmunoassay (RIA) in the supernatant of cellular cultures. 60% of the dhfr⁺ clones were HBsAg⁺. The rate of HBsAg production was relatively weak between 1 and 20 ng/$10^6$ cells per 24 hours.

2) Amplification of the HBV sequences:

It has been obtained in propogating the CHO HBsAg⁺ clones in the presence of methotrexate (MTX), analog of folic acid and dhfr inhibitor. In effect, the resistance to MTX is due principally to an amplification of the number of copies of the dhfr genes which leads to an augmentation of the quantity of the dhfr enzyme. The HBV sequences and the dhfr gene being carried by the same plasmid and thus integrated together in the DNA of the host cells, these are co-amplified with the dhfr sequences in the MTX resistant clones. Like for the dhfr, the augmentation of the number of the copies of the HBV sequence is accompanied by an augmentation of the synthesis of HBsAg by the cell.

Figure 3:
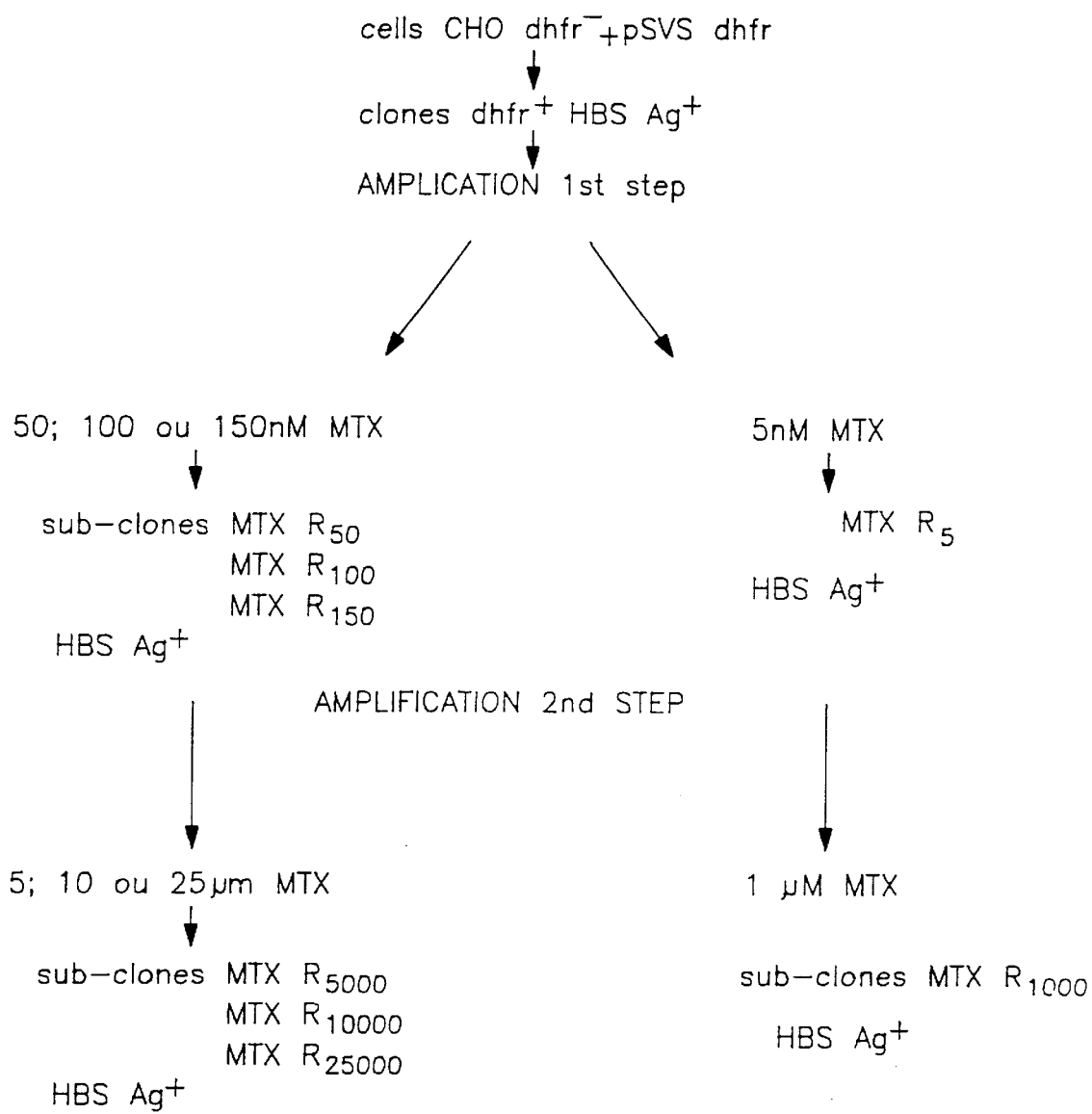
FIG. 3 is a schematic representation of the operations of amplification of DNA sequences coding for the polypeptide immunogen according to the invention in the CHO cells.
Figure 4:
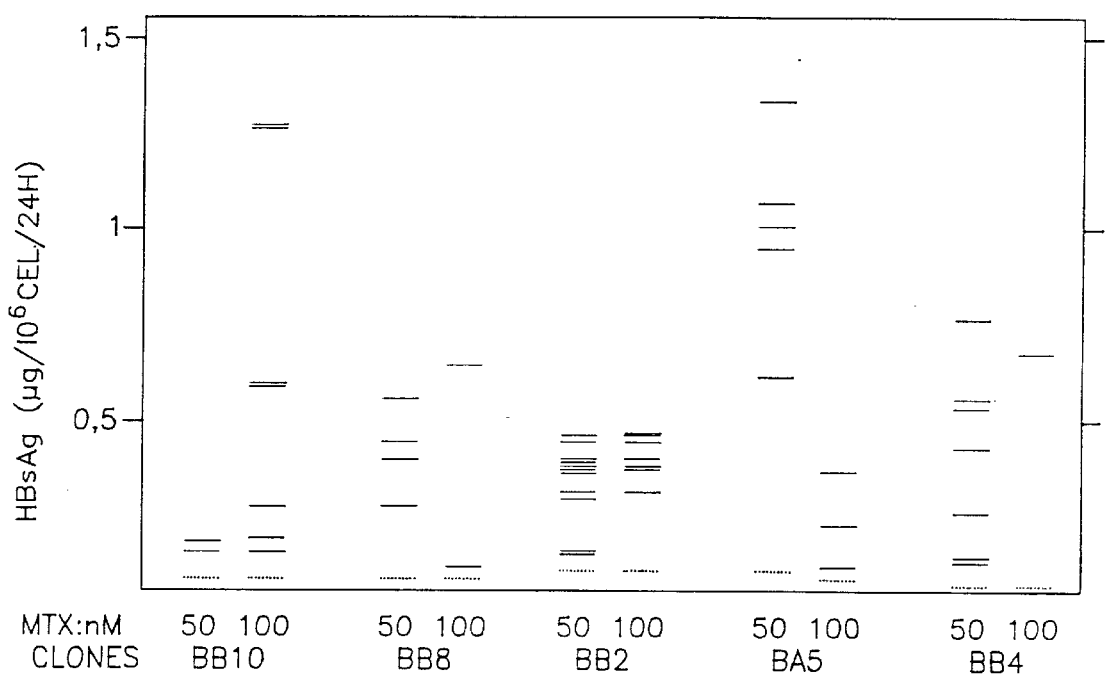
FIGS. 4 and 5 show the results of the gene amplification of the cells previously transformed under the conditions of the process according to the invention.
Figure 5:
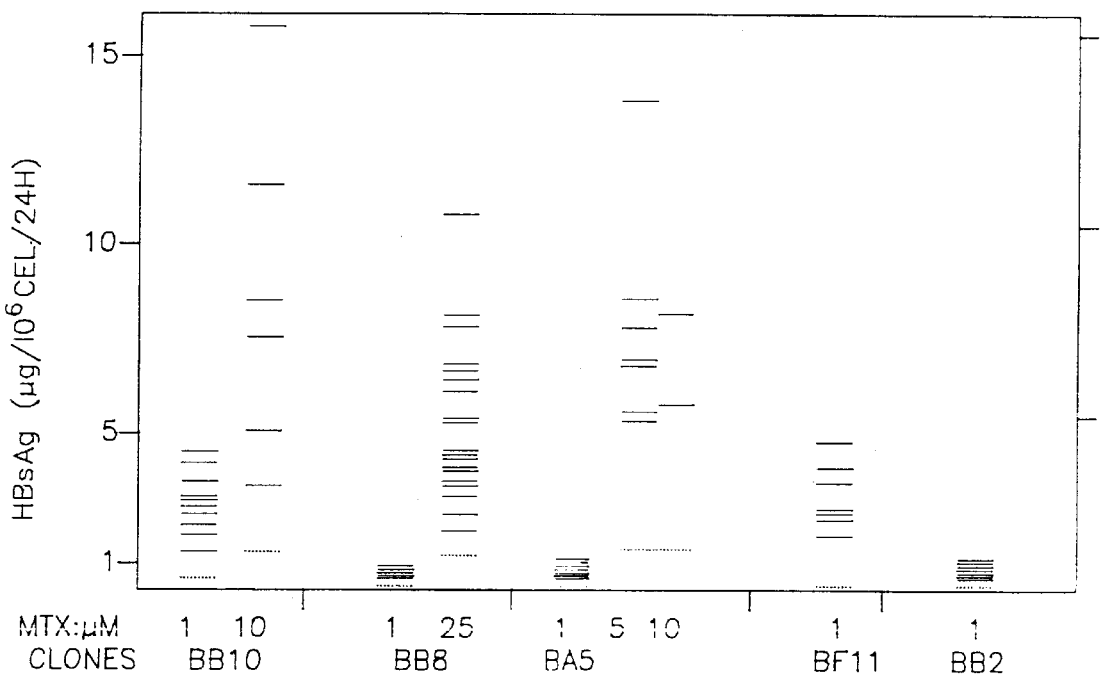

The gene amplification has been effected in two steps according to the strategy described in FIG. 3. FIG. 4 represents the results of the first amplification step and FIG. 5 the results of the second step. This has been effected from the most productive clones, issued from the first step. In FIGS. 4 and 5, the dotted bars represent the rate of synthesis of HBsAg before amplification and the bars in solid lines after amplification. The concentrations of MTX are reported in these figures. They were 50, 100 or 140 nM in the first step and 1.5, 10 or 25 micro-M in the second. In total, around 150 MTX resistant clones have been screened for the production of HBsAg. As shown in FIGS. 4 and 5, the amplification of HBsAg production was highly variable from one clone to another, in the first as well as the second step.

The number of copies per cell of the HBV sequence present in different clones has been evaluated according to the hybridization technique on a cellulose filter or analogue, according to the technique called "dot tblot", utilizing as a probe cloned HBV-DNA labeled with $^{32}$P. For one same dose of MTX, this number was extremely variable from one clone to the other, going from 100 to 500.

The organization of the HBV sequences in the cellular clones has been analyzed according to the technique of Southern. The HBV sequences were present in the integrated form; the electrophoresis profiles were reasonably comparable from one clone to another. The differences observed between the selected clones at one same dose of MTX does not permit the explanation of the conflict between the number of copies of HBV-DNA and the level of synthesis of HBsAg (results not reported). A comparable analysis has been effected for the dhfr gene. For one same dose of MTX, the number of copies per cell was equally highly variable from one clone to the other (results not reported). For a given clone, there was a parallel amplification of the HBV and dhfr sequences.

Figure 6:
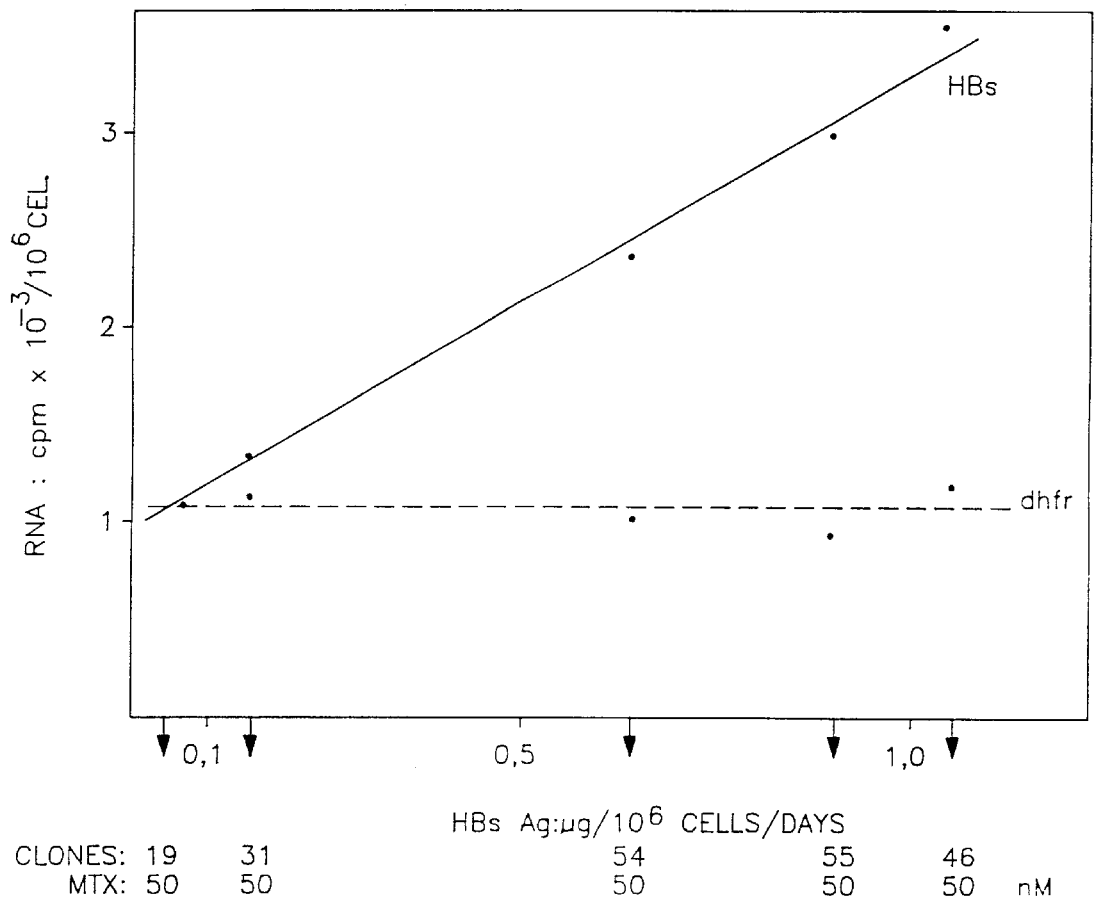
FIG. 6 contains a curve representative of the variation of the quantity of HBsAg antigen produced as a function of the levels of specific HBV-RNAs observable in the producing cells.

The quantity of specific RNAs of HBV has equally been analyzed by molecular hybridization. Contrary to the results obtained for DNA, the quantity specific HBV RNAs was proportional to the rate of HBsAg production (FIG. 6). Moreover, for one same dose of MTX (50 nano-M), the quantity of dhfr specific RNAs was constant in the different clones analyzed (FIG. 6). The specific HBV RNAs have been analyzed according to Northern. Two RNAs, a major one of 2.1 kb, the other minor at 2.5 kb, have been demonstrated. The study of these RNAs by S1 nuclease mapping has shown the existence of a major initiation in the region pre-S at the 3157 position corresponding to the 2.1 kb RNA, the other minor in the SV40 promoter corresponding to the 2.5 kb RNA.

3) Analysis of the HBsAg particles:

The analysis has been effected on the particles produced by the 37BA5. The supernatants corresponding to several harvests of 24 hours obtained in stationary phase have been put together. The HBsAg particles have been purified by two successive ultracentrifugatlions in a CsCl density gradient followed by a velocity ultracentrifugation in a sucrose gradient. The HBsAg particles have a density of 1.20. Observed under the electron microscope, they appeared like spherical particles of a mean diameter of 22 nm, morphologically similar to particles of human origin. No tubular form was observed.

After dissociation of the particles at 100 degrees for 5 minutes in the presence of DTT, the polypeptides have been analyzed by gel electrophloresis on polyacrylamide in the presence of SDS. The gel has been revealed by coloration with silver salts. Three bands have been observed, corresponding to polypeptides of 22,300, 26,100 and 34,000 daltons. The relative intensity of the coloration of these three bands has permitted the evaluation at 54%, 19% and 27% the proportions of the three proteins. After labeling in vivo by $^{35}$S methionine, the purified particles have been immunoprecipitated by an anti-HBs serum, then the proteins were analyzed by electrophoresis. The three polypeptides described above were detected on the autoradiogram and in the same proportions.

The presence of the receptor for pHSA at the surface of the particles has been tested by radioimmunoassay in soliid phase according to the technique of Hansson and Purcell (1979), Infect. Immun. 26, 125), modified by Pontisso et al (J. of Virological Methods 6, 151–159). The detection of this receptor is revealed to be positive in the supernatant as well as on the purified particles (Table 1):

TABLE 1

| | |
|---|---|
| Supernatant of the culture (13 micrograms/ml) | 2,805 cpm |
| Purified particles (12 micrograms/ml) | 1,564 cpm |
| Positive control serum HBe positive | 2,536 cpm |
| Negative control serum HBsAg negative | 678 cpm |

One may equally utilize the technique described by Machida et al (1983), Gastoenterology 85, 268–274.

III—IMMUNIZATION ASSAYS

After addition of aluminum hydroxide $Al(OH)_3$ to the concentration of 0.1%, a preparation of particles has been used to immunize Balb/c mice. As shown in Table II, the immunogenic power of cellular particles is identical to that of the vaccine against hepatitis B, commercialized under the trademark HEVAC B (and obtained from human donors from serums having levels of natural HBsAg). The 50% effective dose is of 0.04 microgram for the cellular particles and of 0.03 microgram for HEVAC B (trademark of the Institut Pasteur).

coding for the protein of the capsid excludes the production of complete infectious viral particles. This vector equally carries a unit of transcription of the gene of murine dhfr which, after introduction into dhfr$^-$, permits them to be multiplied in the presence of MTX by a phenomenon of gene amplification.

Figure 7:
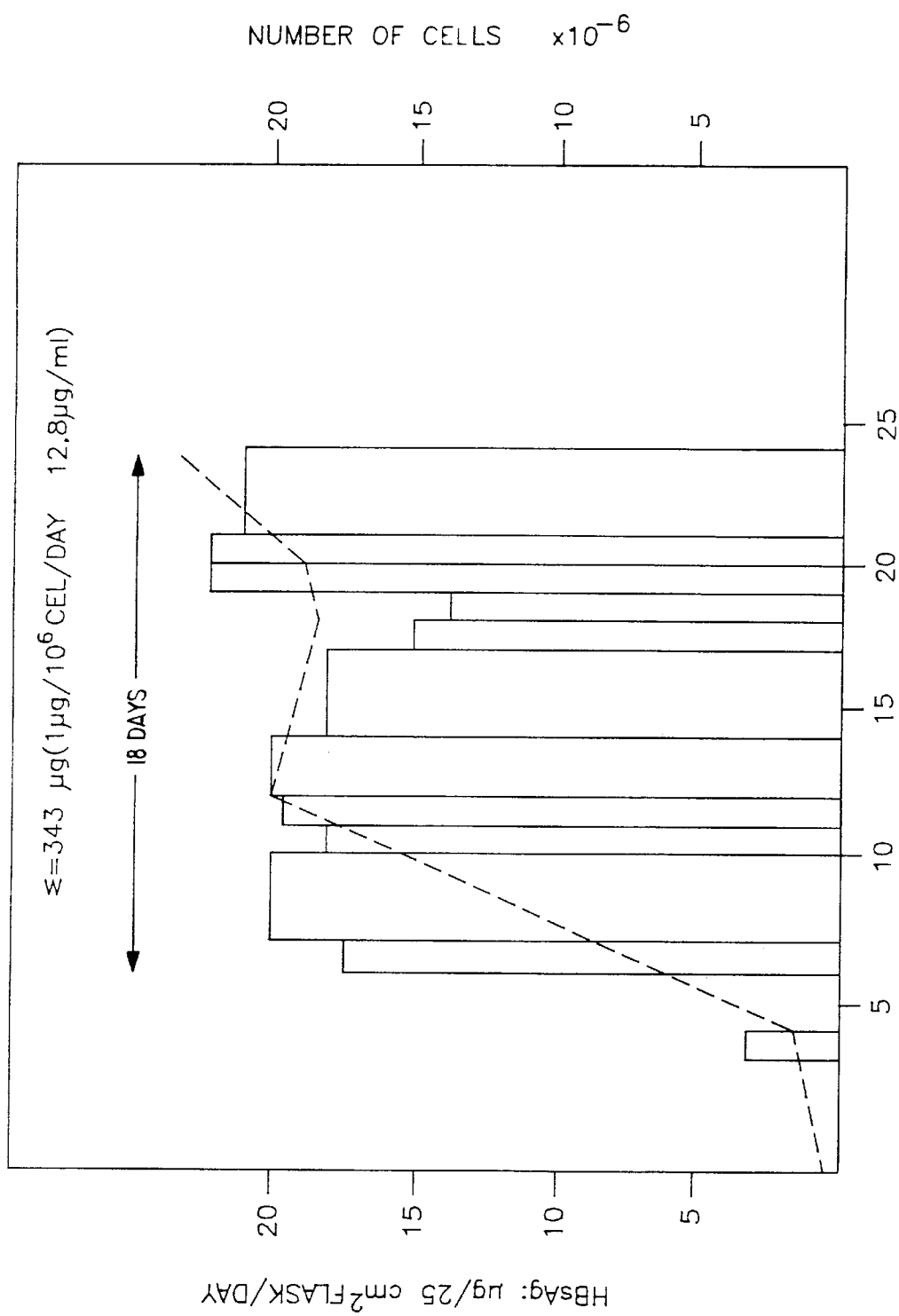
FIG. 7 reports in schematic fashion the successive harvests of the cells in stationary phase.

The technique of amplification by resistance to MTX, utilized here, has permitted the obtaining of clones of CHO cells producing HBsAg particles at a high level. This amplification was variable from one clone to another. In certain cases, the level of synthesis has been multiplied by 1500. For the clone concerned, the rate of production was 15 micrograms/$10^6$ cells per 24 hours. Several clones producing 1 to 10 micrograms of HBsAg/$10^6$ cells per 24 hours were obtained. The rate of HBsAg production expressed per ml and per 24 hours depends on the culture conditions. The values of 10 to 20 micrograms/ml/24 hours could commonly be obtained, values comparable to the HBsAg concentration in the serum of chronic carriers. A kinetic study of the production of HBsAg has shown that this synthesis remains constant in stationary phase for several weeks. FIG. 7 reports the results of successive harvests gathered from cells in stationary phases by periodic renewal of the culture medium over three weeks. Medium without serum may be used for these harvests. Other than the impact on cost price, the use of a medium without serum greatly facilitates the purification of the particles from the cellular supernatant and eliminates possible contaminations of seric origin. The synthesis of HBsAg by CHO clones has proved highly stable even in the absence of MTX. And this over a period of 6 months, around 300 generations. In certain cases, a slight spontaneous increase in HBsAg produced has even been observed. Never a diminution or a loss of the HBsAg production has been observed during gene amplification, and this on around 150 clones tested. These last two observations may be due to the structure of the vector in which the HBV sequences and the dhfr gene were only separated by around 300 bp of pBR322.

The invention consequently permits the obtaining of clones which produce immunogenic particles of a particularly remarkable genetic stability.

A correlation between the number of copies of HBV sequences and the rate of HBsAg synthesis has not been observed. The technique utilized (the "dot blot") permits a global quantification, but does not permit discrimination of the functional sequences. The results obtained may tie

TABLE II

| | Vaccine HEVAC B | | Particles HBsAg CHO | |
|---|---|---|---|---|
| HBsAg Injected doses | Seroconversion >50 µRIA Number of mice | Anti-HBs antibodies Geometric mean µRIA | Seroconversion >50 µRIA Number of mice | Anti-HBs anti bodies Geometric mean µRIA |
| 0.312 micrograms | 20/20 | >388 | 20/20 | >505 |
| 0.078 micrograms | 19/20 | >212 | 14/20 | >87 |
| 0.019 micrograms | 6/20 | >24 | 6/20 | >24 |
| 0 controls | 4/20 | | | |
| | DE$_{50}$0.04 micrograms | | DE$_{50}$0.03 micrograms | |

µRIA = units defined in the AUSAB test commercialized by ABBOTT

It results then from what has preceded that the vector pSVS dhfr permits, after integration into the cellular DNA, the synthesis and excretion of the empty envelopes of the HBV virus in the form of 22 nm particles. The elimination of a great part of the HBV genome and in particular the gene explained by the appearance of deletions and rearrangements in the vector during the transfection and amplification. This hypothesis is supported by the complexity of the electrophoretic profiles of the integrated HBV and dhfr sequences. Many of these sequences are probably nonfunctional. On the other hand there is perfect proportionality between the level of HBsAg synthesis and the quantity of specific HBV-RNAs. This demonstrates that the augmentation of the HBsAg synthesis observed is in fact due to an augmentation in the transcription of the HBV sequences, due in part very probably to an augmentation of the number of functional copies. This result also shows that the evaluation of the number of copies of an amplified genes whether it be by dot blot or electrophoretic analysis is not the best test to evaluate the number of effective copies in a cellular clone. On the other hand, the quantification of the specific RNAs reflects perfectly the functional copies. This quantification takes on full interest in cases where the protein produced is not easily measurable.

The invention therefore concerns more particularly clones containing a dose of HBV-RNA of at least $2\times10^3$ cpm/$10^6$ cells in the system of measure such as has been described above for a probe having a specific activity of $10^6$ cpm/microgram (labeled with $^{32}$P), Two specific HBV-RNAs have been demonstrated. The initiation of the major transcript of 2.1 kb has been localized in the pre-S region at the position 3157. This is in agreement with the results of Catteneo et al (1983) Nature, vol. 305, 336–338, who have localized the initiation of the transcription of the S gene at this position. The minor RNA of 2.5 kb is initiated in the promoter of SV40. This RNA may be the mRNA of the polypeptide of 34,000 (GP34) present in the particles. It is therefore probable that the synthesis of GP34 in a large quantity (27% of the polypeptides of the particles) is due to the utilization of the early promoter of SV40 including the repeated 72 bp and placed 'upstream' of the pre-S region.

The utilization of a radioimmunoassay has shown that the particles synthesized by the CHO cells bearing the pHSA receptor. According to Machida et al (1983) Gastroenterology 85, 268–274, this receptor might be carried by the polypeptides GP31 and GP35. It is therefore probable that in our system the receptor is carried by GP34. The observed existence of only one polypeptide, and not two, carrier of the pHSA receptor in particles of cellular origin is not explained. It is possible that, contrary to seric particles, the glycosylation in the CHO cells is homogeneous.

The HBsAg particles of 22 nm synthesized by the CHO cells have the same immunogenicity as HEVAC B which is a preparation of particles of seric origin. The rates of HBsAg production obtained are compatible with an industrial utilisation. The presence of the pHSA receptor at the surface of these particles is a supplementary argument for the utilization of this system for the manufacture of a vaccine against hepatitis B.

As such, the invention concerns any vaccine composition against viral hepatitis B containing an effective dose of particles according to the invention, notably from 3 to 6 micrograms of protein/ml (unitary dose), in association with a pharmaceutical vehicle appropriate to the chosen mode of administration, notably parenterally.

We claim:

1. A vector for transforming CHO dhfr$^-$ cells, wherein said vector comprises:
    a) a first DNA sequence encoding the pre-S region of the hepatitis B virus genome;
    b) a second DNA sequence encoding the S region of the hepatitis B virus genome;
    c) a first promoter, wherein said first promoter is the SV40 early promoter, and wherein said first promoter directly promotes the expression of said first and second DNA sequences;
    d) a marker gene sequence, wherein said marker gene is the dhfr gene; and
    e) a second promoter, wherein said second promoter promotes the expression of said marker gene sequence, and wherein said second promoter is obtained from mouse mammary tumor virus.

2. A CHO dhfr$^-$ cell line, wherein said cell line is transformed by the plasmid pSVS.

* * * * *